(12) United States Patent
Liu et al.

(10) Patent No.: US 8,069,011 B2
(45) Date of Patent: Nov. 29, 2011

(54) GENERATING DAMAGE PROBABILITY-OF-DETECTION CURVES IN STRUCTURAL HEALTH MONITORING TRANSDUCER NETWORKS

(75) Inventors: Bao Liu, Cupertino, CA (US); Fu-Kuo Chang, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 662 days.

(21) Appl. No.: 12/103,584

(22) Filed: Apr. 15, 2008

(65) Prior Publication Data
US 2008/0255804 A1    Oct. 16, 2008

Related U.S. Application Data

(60) Provisional application No. 60/912,112, filed on Apr. 16, 2007.

(51) Int. Cl.
*G06F 17/18* (2006.01)

(52) U.S. Cl. .......... 702/181; 702/35; 702/121; 702/122; 702/123; 702/182; 702/183; 702/184; 702/185; 702/186; 702/187; 702/188; 702/189; 702/190; 73/577

(58) Field of Classification Search .......... 702/121–123, 702/181–190, 35; 73/577
See application file for complete search history.

(56) References Cited

U.S. PATENT DOCUMENTS

2006/0079747 A1*   4/2006   Beard et al. .................. 600/407

OTHER PUBLICATIONS

Bilski Guidelines Part 1.*
Bilski Guidelines Part 2.*

* cited by examiner

*Primary Examiner* — Sujoy Kundu
(74) *Attorney, Agent, or Firm* — Innovation Counsel LLP

(57) ABSTRACT

A method for automatically creating a probability of detection (POD) curve of an entire network of transducers monitoring and detecting damage in a structure is based on the POD of each of the individual actuator-sensor paths. These individual path PODs may be generated in different ways, such as by experimentation or simulation. This technique makes it possible to create the POD curve of a structural health monitoring (SHM) system for the detection of damages in structures.

14 Claims, 2 Drawing Sheets

GENERATING DAMAGE PROBABILITY-OF-DETECTION CURVES IN STRUCTURAL HEALTH MONITORING TRANSDUCER NETWORKS

RELATED APPLICATIONS

This application claims the benefit of U.S. provisional patent application No. 60/912,112, entitled "Structural Health Monitoring System And Methods For Use," filed Apr. 16, 2007, the entire disclosure of which is incorporated herein by reference.

TECHNICAL FIELD

This invention relates generally to the field of structural health monitoring (SHM). More specifically, this invention relates to methods for creating probability of detection (POD) of damage curves for transducer networks of SHM systems adapted to detect damage in structures.

BACKGROUND

Probability of detection (POD) is a basic tool used to comprehensively characterize the damage detection capability of non-destructive testing (NDT) techniques. Recently, the concept of POD has also received great interest in SHM research and applications. In addition to providing an evaluation of the damage detection capability of a SHM system, the POD value at the minimum detectable damage size (i.e., a "critical damage size" $1_{dmg}$, which may, for example, characterize the diameter of a damage in a composite structure, or in the case of metal structures, the length of a crack damage therein) is also a valuable parameter in transducer network layout design. Therefore, determination of the POD of a SHM system is of great importance.

Many traditional NDT techniques, such as eddy current testing, demonstrate the nature of single point measurement. That is, for each measurement, the sensor measures only the structural condition within a localized or relatively small area. In such cases, POD curves can be generated by creating real damages of different sizes. However, such traditional testing approaches may be impractical for a SHM sensor network if a large structure area is monitored, since it may not be possible or practical to create and measure damages of different sizes at a large number of locations over a large area.

To overcome the above difficulty, a computational POD curve generation method has been proposed by Shawn and Chang (U.S. Prov. Pat. App. Ser. No. 60/912,112) based on simulated damages characterized by varying size radius at distributed locations on a structure. However, such purely computational methods may not be capable of performing detailed analysis based on actual waveform signal structure. A method is therefore developed in the present invention that creates the damage detection POD curve for the entire network of transducers of a SHM system over a large area structure by synthesizing PODs based on actual signal waveforms obtained from actual test data of individual actuator-sensor paths defined by associated actuator-sensor transducer pairs.

SUMMARY

In accordance with the present disclosure, a method is provided for automatically creating a POD curve for an entire network of transducers for monitoring and detecting damage in a structure based on the POD of each of the individual actuator-sensor paths. These individual path PODs may be generated in different ways as described in detail below. This technique makes it possible to create the POD curve of a SHM system for the detection of damages in structures.

In one example embodiment, a method for determining the probability of detection (POD) of a damage in a structure with a networked configuration of transducers placed at respective locations on the structure comprises: Specifying parameters descriptive of the structure on which the network of transducers is to be placed; specifying a minimum desired POD of damage detection, $POD_d$; generating a plurality of different transducer position layouts for the network, each layout being determined by the number and placement of transducers therein; generating the POD curve for each sensor layout using a POD determination method; finding from the POD curve of each sensor layout the damage size that corresponds to $POD_d$, denoted by $l_k$, for k=1, 2, ..., K, where K denotes the total number of the sensor layouts; and generating the curve of sensor layout density as a function of the values of $l_k$ found.

A better understanding of the above and many other features and advantages of the novel methods for creating SHM POD curves of the present disclosure may be obtained from a consideration of the detailed description of some example embodiments thereof below, particularly if such consideration is made in conjunction with the several views of the appended drawings, wherein like elements are referred to by like reference numerals throughout.

DETAILED DESCRIPTION

In a network of sensors and actuators comprised of elastic wave transducers (e.g., piezoelectric, lead-zirconate-titanate (PZT) transducers), the minimum measurement unit or building block is a single actuator-sensor path. A network of transducers, no matter how complicated in geometry, may always be decomposed into individual actuator-sensor paths defined by associated pairs of transducers. Therefore, if the POD of damage of a single path at a position within the neighborhood of the path can be determined, it is possible to synthesize the POD of the entire network.

More specifically, if the POD for a single path is determined first, then the POD at any position in the network can then be computed probabilistically. In practice, the POD values corresponding to a critical damage size $1_{dmg}$ is of central interest. The methods of the present invention can be used to directly predict the probability of detecting damage in structures that are equal or greater than the critical damage size characterized by $1_{dmg}$.

According to an embodiment of the present invention, a method for determining the POD of a transducer array comprises two major components: 1) Determining the POD of a single path, and 2) computing the network POD. A detailed description of each of these components and example methods for carrying them out is given below.

Single Path POD

Figure 1A:
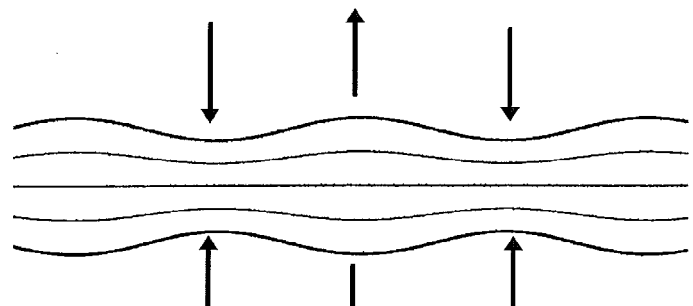
FIGS. 1A and 1B are schematic illustrations of the surface displacement of symmetric and anti-symmetric elastic waves propagating in a structure, respectively.
Figure 1B:
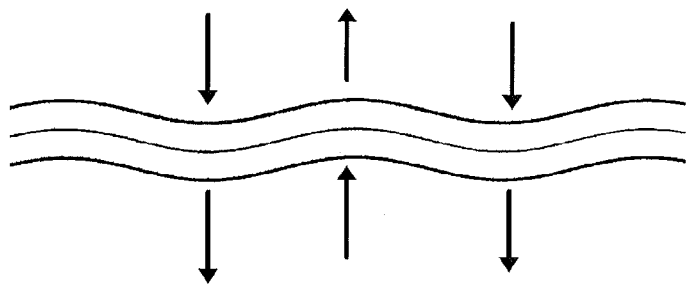

First, the concept of a "detectable damage" is defined. In plate-like structures, propagating elastic waves are referred to as Lamb waves, in which the particle motion lies in the plane defined by the plate normal and the direction of wave propagation, and are typically characterized as "symmetric" or "anti-symmetric" in amplitude displacement about the midpoint of the plate. A symmetric mode wave, also known as an extensional mode, exhibits surface displacement on opposing sides of the midline of the plate that is substantially a mirror image displacement, as illustrated in FIG. 1A, which schematically illustrates a fundamental symmetric mode. By contrast, an anti-symmetric mode, also known as a flexural mode, exhibits substantially transverse displacements in the same directions on both sides of the plate, as illustrated in FIG. 1B. Both symmetric and anti-symmetric modes may occur in successive "orders" of discrete modes, determined by certain boundary conditions. For simplicity, the following discussions are made in terms of the zero order of each of the symmetric and anti-symmetric modes.

The anti-symmetric flexural mode has a significantly lower transverse restoring force because there is substantially no compression, as in the extensional symmetric mode, and therefore, the phase velocity of propagation is typically lower than that of the symmetric mode. Thus, a pulse of a symmetric mode wave will typically exhibit a shorter time-of-arrival at a sensor transducer than that of the anti-symmetric mode thereof.

For a "baseline" elastic wave signal, i.e., an elastic wave propagated between two transducers in a baseline structure (i.e., one having no damage in it), the respective first arrivals of the zero-order symmetric and anti-symmetric mode may each be detected within a selected time window. Wave packets arriving immediately after the respective first arrivals of each type of wave may be considered as "scattering signals," i.e., as arriving from reflections from damages that are not in the direct path between the two transducers.

For each of the two modes, the signal segment containing the first arrival and the corresponding scattering wave packet may first be selected as a "featured," i.e., most relevant, component of a signal. The corresponding segments (for both the symmetric and anti-symmetric modes) of a "current" signal (i.e., as opposed to a baseline signal) may also be selected as the featured components of the current signal.

Let $e_b^{S0}$ denote the energy in a selected time window of the featured component of the baseline signal data corresponding to the zero order symmetric mode, and $e_c^{S0}$ denote that of the current signal data, respectively. Then, the following damage index $I_{S0}$ may be defined for the symmetric mode of each actuator-sensor path:

$$I_{S0} = \sqrt{\frac{|e_b^{S0} - e_c^{S0}|}{e_b^{S0} + e_c^{S0}}}. \tag{1}$$

A similar damage index $I_{A0}$ may be defined for the anti-symmetric mode as:

$$I_{A0} = \sqrt{\frac{|e_b^{A0} - e_c^{A0}|}{e_b^{A0} + e_c^{A0}}}. \tag{2}$$

If the current signal is collected when damage does exist in the neighborhood intersecting the individual actuator-sensor path, the symmetric and/or the anti-symmetric modes of the current signal will generally be different from those of the corresponding baseline signal. Where a damage is located adjacent to the direct line of a path, but does not directly interfere with (i.e., attenuate) the direct signal, the elastic wave energy may scatter from the damage site and be detected at the receiving transducer (i.e., sensor) by traveling along an indirect path, as indicated by the path segments R1 and R2 in FIG. 2. In such cases, a second, delayed signal may arrive in the same time window, as described above. However, the direct path signal and delayed scattered signal may then coherently interfere with each other, thereby causing a change in the energy $e_c^{S0}$ of the current signal in the selected time window. Therefore, equations (1) and (2) remain valid without loss of generality.

The amount of the differences characterized by $I_{S0}$ and $I_{A0}$ will be dependent on the size and severity of the damage, as well as its location with respect to the path. Respective threshold values may be defined to determine whether a damage is detectable. Let $T_S$ and $T_A$ be the respective thresholds defined. Then, by definition, damage is deemed to have been detected if $$I_{S0} > T_S \text{ and/or } I_{A0} > T_A. \tag{3}$$

With the above definition, the POD of an individual actuator-sensor path may then be determined using one of the following methods:

1) By an experimental method with simulated damages on a sample structure. The simulated damage may be created by bonding stiff metal or a damping patches to the structure. Each of these types of simulated damage produces a different effect on both the directly propagating and scattered signals.
2) By an experimental method with real damages on a sample structure. This is a more destructive method, as the sample structure is not reusable, but may more accurately represent that which may be obtained in actual implementation.

Figure 2:
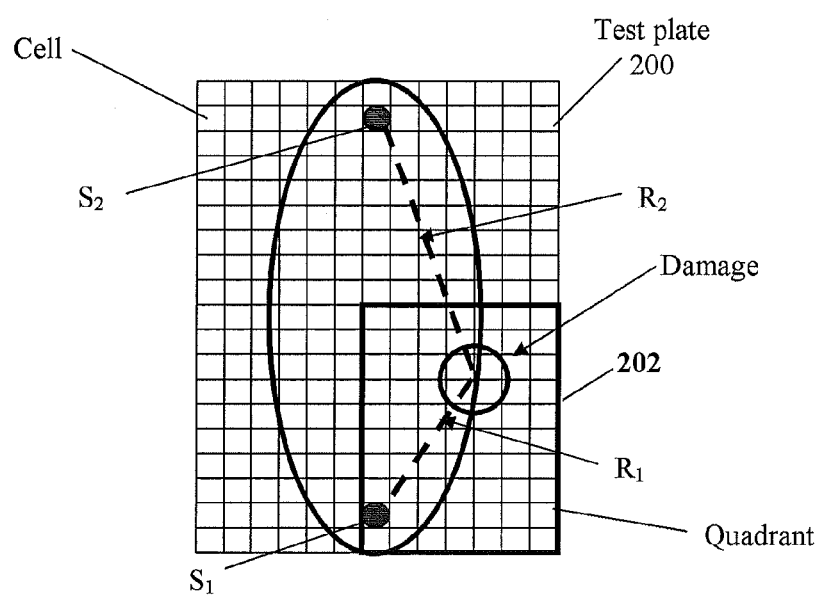
FIG. 2 is a schematic illustration of an example embodiment of a test structure for experimentally determining the probability of detection (POD) of damage therein for a single actuator-sensor path on the structure in accordance with the present disclosure.

Using the above methods, a POD database can then be established as follows. It may be noted first that, as illustrated in FIG. 2, the path between the two transducers S1 and S2 on the test plate 200 is symmetric, and as a result, in either of the above methods, it is necessary to simulate or create damages in only a quarter of the effective region of a path (e.g., the quadrant 202 indicated in FIG. 2). In implementation, damages of different sizes may be created or simulated at each cell of the grid a selected number of times, for example X times. However, damage detection, as defined by equation (3), may result in identifying a damage at that location only Y times. The signal detection POD for a damage at each location may then be computed as the total number of detected damages divided by the total number of simulated or created damages, i.e., the POD=Y/X, expressed as a percent. In implementation, transducers may be placed at various distances, the grid may be sparse and the cell size can be roughly set to the same order of the damages to be monitored, e.g., 1 inch (1") to 3" for impact-type damages. The POD at locations where no damage is created may be obtained by interpolation. Thus, a database can be established that provides a probability of detection between two transducers defining an actuator-sensor path for damages of different types and sizes at various locations on a structure in relation to that actuator-sensor path.

Thus, to generate the POD of a sensor network, the individual path POD for different path lengths may first be determined, as above, where, for example, path lengths may vary from 4" to 15", in 1" increment. As in traditional non-destructive testing (NDT) processes, this process of POD generation needs a considerable amount of testing. However, once created, the POD results for different path lengths and damage locations may then be used to form a standard database. This database may be used for evaluation of the POD of various designs of transducer networks, and for transducer layout optimization for various applications. Individual path POD test results for different structure materials and thicknesses may also be included to further improve the database. The accuracy of the sensor network POD will be improved by continually adding new individual path POD results to the database.

Transducer Network POD

To determine the probability of detection (POD) of damage of a SHM transducer network on a structure, i.e., a network comprising a plurality of transducer paths, a grid is first defined over the area to be monitored by the network. The cell size of the grid may be set in the same way as that for the individual path POD above. Two types of PODs may be defined for the SHM sensor networks: 1) the POD at a specific cell of the grid, and 2) the POD of the entire monitored area of the structure. Once the respective PODs at all of the cell locations of the monitored structure are obtained, the POD of the entire monitored area of the structure may be defined simply as the average of the PODs at all of the cell locations.

Figure 3:
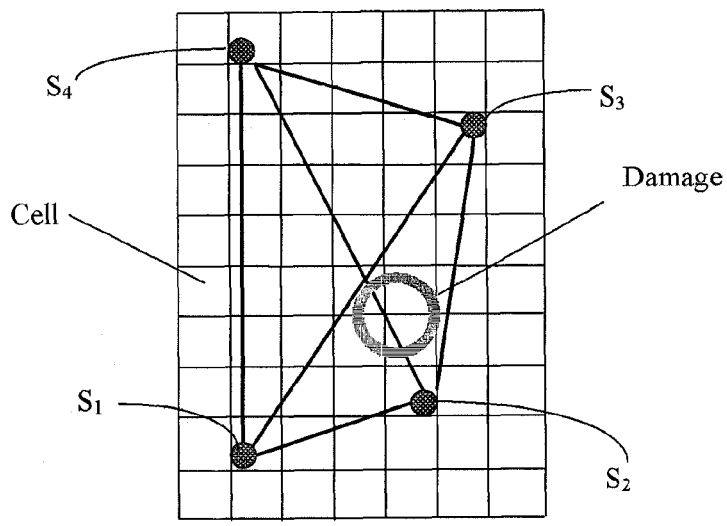
FIG. 3 schematically illustrates an example embodiment of a network of transducers disposed on a structure for detecting damage therein in accordance with the present disclosure; and, FIG. 4 is a process flow diagram of an example embodiment of a method for determining the transducer density on a structure for a given desired minimum POD at various damage sizes in accordance with the present disclosure.

As illustrated in FIG. 3, each cell may have a number of neighboring paths (e.g., six paths in the example embodiment of FIG. 3). After the signal detection PODs of the individual paths are obtained as above, the POD of the network of damage at a specific cell may be obtained by computation using certain rules. The following are two examples of the rules that can be used:

1) Use the maximum signal detection POD of all the neighboring paths of a particular cell as the damage detection POD of the network at that cell.
2) Use the second maximum signal detection POD (according to equations (1), (2) and (3)) above of all the neighboring paths of a particular cell as the damage detection POD of the network at that cell. This means that damage is said to be detectable by a network at a certain POD value if at least two neighboring paths can detect this damage. Compared with rule 1) above, this rule may reduce the false positive detection by reducing the sensitivity.

The computational method described above is merely an example thereof, and different computational rules may be defined, depending on the particular application at hand.

After the POD at all of the cell locations of the monitored structure are computed, the POD of the whole network may then be defined as the average of the PODs at all the locations.

Transducer Density Versus Damage Size

In planning the layout of transducers for a SHM system, it is often desirable to know the relationship between the transducer density and the detectable damage size at a desired value of POD (e.g., 90%). It may also be desirable to determine the system cost, based on the transducer density required to detect the minimum detectable damage size. The transducer density can be specified as the number of transducers per unit area for a given layout. Finding the relationship between the transducer density and the minimum detectable damage size is a direct application of the POD curve of the layout, which can be carried out as follows:

Step 1: Specifying a structure on which a network of transducers is to be placed;

Step 2: Specifying a minimum desired value of POD of damage detection, denoted by $POD_d$ (for example, $POD_d$ may be a 90% probability of detecting damage);

Step 3: Generating a plurality of transducer position layouts for the network, each layout being determined by the number and position of the transducers forming the network;

Step 4: Generating the POD curve for each sensor layout using the POD determination method described above;

Step 5: Finding from the POD curve of each sensor layout the damage size that corresponds to $POD_d$, denoted by $l_k$, for k=1, 2, ..., K, where K denotes the total number of the sensor layouts; and, Step 6: Generating the sensor density layout curve as a function of $l_k$ using the results of Step 5.

Figure 4:
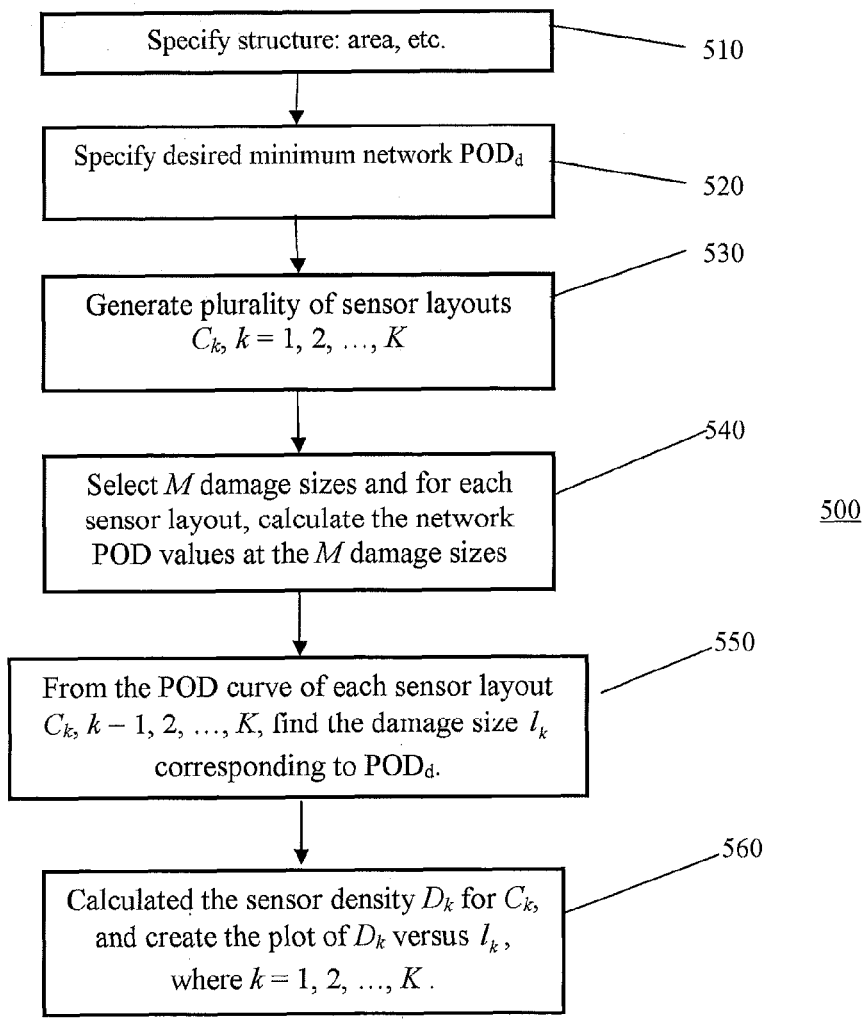

More specifically, FIG. 4 is a process flow diagram of a method 500 for determining the transducer density on a structure for a given desired minimum probability of detection, according to an embodiment of the present invention.

The method 500 begins by specifying the structure to be monitored (step 510). The specification includes at least the geometry and the area of the structure, and may include other structure information, such as the area and location of cutouts, stiffeners, regions with varying thickness, and the like. Next, the minimum desired network POD ($POD_d$) is specified (step 520). For example, the desired $POD_d$ may be set at 90%, 95%, and so on. Then, for the specified structure defined in block 510, a plurality of sensor layouts $C_k$, where k=1, 2, ..., K, is defined (block 530).

A number M of damage sizes $d_m$ is then selected (step 540), where m=1, ..., M. For each sensor layout $C_k$, k=1, 2, ..., K, the POD is calculated for all of the M damage sizes (step 540) using the methods described above, such as, for example, relying on a single path POD in a database and applying it to the sensor layout.

From the POD curve generated above for the sensor layout $C_k$, where k=1, 2, ..., K, the damage size corresponding to $POD_d$, denoted by $l_k$, is picked out (step 550). The sensor density of $C_k$, k=1, 2, ..., K, is calculated as the number of transducers divided by the structure area. Denote by $D_k$ the sensor density for $C_k$, where k=1, 2, ..., K. Then, the plot of $D_k$ versus $l_k$, where k=1, 2, ..., K, is created, which shows the relationship between the transducer density and the detectable damage size at the desired POD level (step 560).

Although the present disclosure has been described with reference to certain specific exemplary embodiments thereof, it will be understood by those skilled in the art that a variety of modifications and variations may be made to these without departing from the spirit and scope of the present disclosure, as defined in the appended claims and their functional equivalents.

What is claimed is:

1. A method for determining a probability of detection (POD) of a damage in a structure with a network of transducers placed at respective locations on a structure, the method comprising:

specifying parameters descriptive of the structure on which the network of transducers is placed;

specifying a minimum desired POD of damage detection, $POD_d$;

generating, in a digital computer or controller, a plurality of different transducer position layouts for the network, each layout being determined by the number and placement of the transducers therein;

in the digital computer or controller, generating a POD curve for each layout using a POD determination method;

in the digital computer or controller, finding from the POD curve of each layout the damage size that corresponds to $POD_d$, denoted by $l_k$, for k=1, 2, ..., K, where K denotes the total number of the layouts; and, in the digital computer or controller, generating a layout density curve as a function of the values of $l_k$ found.

2. The method of claim 1, wherein the descriptive geometry parameters of the structure include at least the dimensions and area of the structure on which the network of transducers is placed.

3. The method of claim 1, wherein the specified $POD_d$ is characterized by a dimension $l_k$, where $l_k$ is one or more of the group consisting of a radius, a diameter, a length and a depth of the damage.

4. The method of claim 1, wherein the generating of the plurality of different transducer position layouts is based on parameters corresponding to one or more of the group consisting of the geometry of the structure, the maximum propagation length of elastic waves in the structure, a minimum size of damage detectable, and a desired POD of the minimum damage size.

5. The method of claim 1, wherein:
the transducers of the array are arranged in associated pairs, each comprising an actuator transducer and a sensor transducer;
a signal is generated by each actuator transducer of each pair that propagates as an elastic wave through the structure and is detected by the sensor transducer thereof; and
the network POD of the damage is the average of the POD of a damage of all of the associated pairs of transducers of the network.

6. The method of claim 5, wherein the POD of a damage by a selected pair of the associated pairs of transducers is based on a database acquired on a test structure by:
transmitting a test signal from the actuator transducer of the selected pair to the sensor transducer thereof at a time when no damage is present in the structure;
sensing and measuring the signal transmitted:
placing a simulated or a real damage at a selected location on the test structure;
retransmitting the test signal from the actuator transducer of the pair to the sensor transducer thereof;
sensing and measuring the retransmitted signals;
measuring the effect of the damage at the selected location on the retransmitted signal;
calculating an index for the selected pair of transducers and the selected damage location comprising the difference between the test signal when no damage is present at the selected location and the test signal when the damage is present at the selected location;
selecting a threshold value of the index, wherein damage is determined to be detected by the selected pair if the index measure exceeds the selected threshold;
repeating the preceding steps at each of a plurality of selected damage locations on the structure and for a number of times sufficient to establish a POD of a damage at each of the selected damage locations by the selected pair, the POD being defined as the ratio of test measurements corresponding to the selected location when the index of the pair is greater than the selected index threshold divided by the total number of test measurements corresponding to the selected damage location made by the selected pair; and
repeating the preceding steps for each of the associated pairs of transducers.

7. The method of claim 6, wherein the index is based on a measure of the difference in the energy of the signal detected by the sensor transducer of the selected pair corresponding to a baseline signal detected when no damage is present in the structure and the energy of a current signal detected by the sensor transducer when the damage is present in the test structure.

8. The method of claim 7, wherein the network probability of detection of damage is determined on the basis of the layout of the network transducers and the single transducer pair probability of detection database.

9. A method for determining the probability of detection (POD) of damage of a structural health monitoring (SHM) transducer network comprising a plurality of transducers and transducer paths and disposed on an area of a structure to be monitored thereby, the method comprising:
defining a rectangular grid over the monitored area of the structure, the grid containing a plurality of cells, each cell containing a plurality of neighboring transducer paths;
measuring the signal detection POD of each transducer path of each cell of the grid;
in a digital computer or controller, computing the POD of damage of the network at a specific cell of the grid in accordance with one or more of:
using the maximum signal detection POD of all of the neighboring paths of the specific cell as the POD of the network at that cell, and
using a second maximum signal detection POD of all the neighboring paths of a particular cell as the POD of the network at that cell, wherein the second maximum signal detection POD is based on the respective energies in a selected time window of featured components of baseline and current signal data corresponding to the respective zero order symmetric and asymmetric modes thereof; and
defining the POD of damage of the entire monitored area of the structure as the average of the PODs of all of the cells of the grid.

10. A method for determining the area density of transducers in a transducer network-based structural health monitoring (SHM) system as a function of damage size, the method comprising:
specifying a structure on which a network of transducers is to be placed;
specifying a desired minimum probability of detection (POD) of a damage for the network of transducers;
generating, in a digital computer or controller, a plurality of position layouts for the transducers forming the network, each layout being determined by the respective positions of a selected number of transducers forming the network;
specifying a plurality of values of damage size in a range of values;
in the digital computer or controller, generating for each layout the network POD at the specified values of damage size;
in the digital computer or controller, generating for each layout a network POD curve by interpolating the generated network POD values;

in the digital computer or controller, finding for each layout the damage size that corresponds to the desired minimum POD from the network POD curve;

in the digital computer or controller, computing the average transducer area density of each layout by dividing the number of transducers in the layout by the area of the monitored structure; and in the digital computer or controller, creating a plot of the transducer densities versus the damage sizes that correspond to the desired minimum probability.

11. A structural health monitoring system utilizing the method of claim 1.

12. A structural health monitoring system utilizing the method of claim 6.

13. A structural health monitoring system utilizing the method of claim 9.

14. A structural health monitoring system utilizing the method of claim 10.

* * * * *